(12) United States Patent
Weldemariam et al.

(10) Patent No.: US 10,963,045 B2
(45) Date of Patent: Mar. 30, 2021

(54) SMART CONTACT LENS SYSTEM WITH COGNITIVE ANALYSIS AND AID

(71) Applicant: International Business Machines Corporation, Armonk, NY (US)

(72) Inventors: Komminist Weldemariam, Nairobi (KE); Shikhar Kwatra, Morrisville, NC (US); Sushain Pandit, Austin, TX (US); Abdigani Diriye, Nairobi (KE); Andrew Kinai, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 349 days.

(21) Appl. No.: 15/962,168

(22) Filed: Apr. 25, 2018

(65) Prior Publication Data
US 2019/0332168 A1    Oct. 31, 2019

(51) Int. Cl.
*G06F 3/01*    (2006.01)
*G02B 27/01*   (2006.01)
(Continued)

(52) U.S. Cl.
CPC ............. *G06F 3/013* (2013.01); *A61B 3/112* (2013.01); *A61B 5/11* (2013.01); *A61B 5/14532* (2013.01);
(Continued)

(58) Field of Classification Search
None
See application file for complete search history.

(56) References Cited

U.S. PATENT DOCUMENTS 8,190,021 B2    5/2012  Wang et al.
9,256,784 B1 *  2/2016  Taylor ............... G06K 9/00597
(Continued)

FOREIGN PATENT DOCUMENTS

EP      2687898 A1      1/2014
WO  2015/194077 A1     12/2015

OTHER PUBLICATIONS

Li, Q., et al., "From "Mission: Impossible"to mission possible: Fully flexible intelligent contact lens for image classification with analog-to-information processing", 2017 IEEE International Symposium on Circuits and Systems (ISCAS), May 28-31, 2017, 4 pages, http://ieeexplore.ieee.org/stamp/stamp.jsp?tp=&arnumber=8050607&isnumber=8049747.
(Continued)

*Primary Examiner* — Christopher Braniff
(74) *Attorney, Agent, or Firm* — Scully, Scott, Murphy & Presser, P.C.; Shimon Benjamin (57) ABSTRACT

A smart lens system may include a hardware processor coupled to a smart contact lens, which may include a microprocessor, an image capturing sensor, and a wireless communication interface. The smart lens system may determine reading factors associated with a user with respect to the user reading content item, based on data related to the user's physiological movements captured by the smart contact lens. The reading factors may include a user's cognitive state determined at least from analyzing data representing the user's physiological movements. Responsive to determining that the user's cognitive state is above a threshold value, the smart lens system may generate an assistive action associated with the content item and transmit a signal to at least one assistive device to perform the assistive action. The assistive device performs the assistive action responsive to receiving the signal.

20 Claims, 6 Drawing Sheets

(51) Int. Cl.
　　　A61B 5/16　　(2006.01)
　　　G02C 7/04　　(2006.01)
　　　G02C 11/00　 (2006.01)
　　　A61B 5/145　 (2006.01)
　　　A61B 3/11　　(2006.01)
　　　A61B 5/11　　(2006.01)
　　　A61B 5/00　　(2006.01)
　　　G06F 16/34　 (2019.01)

(52) U.S. Cl.
　　　CPC .............. *A61B 5/163* (2017.08); *A61B 5/165* (2013.01); *A61B 5/6821* (2013.01); *G02B 27/0172* (2013.01); *G02C 7/04* (2013.01); *G02C 11/10* (2013.01); *G06F 16/345* (2019.01); *G02B 2027/0138* (2013.01); *G02B 2027/0141* (2013.01); *G06F 2203/011* (2013.01)

(56) References Cited

U.S. PATENT DOCUMENTS

| | | | |
|---|---|---|---|
| 2013/0169530 | A1 | 7/2013 | Bhaskar et al. |
| 2015/0073907 | A1 | 3/2015 | Purves et al. |
| 2015/0279117 | A1 | 10/2015 | Schimke |
| 2015/0281411 | A1 | 10/2015 | Markus et al. |
| 2016/0062150 | A1 | 3/2016 | Sako et al. |
| 2016/0091737 | A1 | 3/2016 | Kim et al. |
| 2016/0097940 | A1 | 4/2016 | Sako et al. |
| 2016/0113760 | A1 | 4/2016 | Conrad |
| 2016/0299354 | A1 | 10/2016 | Shtukater |
| 2016/0324451 | A1 | 11/2016 | Young |
| 2017/0023793 | A1 | 1/2017 | Shtukater |
| 2017/0061034 | A1 | 3/2017 | Ritchey et al. |
| 2017/0336641 | A1 | 11/2017 | von und zu Liechtenstein |
| 2017/0365101 | A1* | 12/2017 | Samec ............... A61B 5/4094 |
| 2017/0371184 | A1* | 12/2017 | Shtukater ............ G02C 7/04 |
| 2018/0040056 | A1* | 2/2018 | Mahmoud ........... G06N 5/02 |

OTHER PUBLICATIONS

Whitney, L., "Samsung's 'eye mouse' enables users to control their computer with a glance", CNET, https://wwwww.cnet.com/news/samsungs-eyecan-lets-your-eyes-control-your-computed, Nov. 25, 2014, Accessed on Apr. 24, 2018, 3 pages.

Wikipedia, "Eye Tracking", https://en.wikipedia.org/wiki/Eye_tracking , Last edited on Apr. 9, 2018, Accessed on Apr. 24, 2018, 7 pages.

Creighton, J., "Bionic Contacts: Goodbye Glasses. Hello Vision That's 3x Better Than 20/20", Futurism, https://futurism.com/bionic-contacts-goodbye-glasses-hello-vision-thats-3x-better-than-2020/, Published May 23, 2015, Last updated on Mar. 22, 2018, Accessed on Apr. 24, 2018, 4 pages.

Elgan, M., "Why a smart contact lens is the ultimate wearable", Computerworld, http://www.computerworld.com/article/3066870/wearables/why-a-smart-contact-lens-is-the-ultimate-wearable.html, May 9, 2016, Accessed on Apr. 24, 2018, 6 pages.

Edwards, L., "Smart contact lenses: What's the story so far?", Pocketlint, http://www.pocket-lint.com/news/137530-smart-contact-lenses-what-s-the-story-so-far, May 5, 2016, Accessed on Apr. 24, 2018, 7 pages.

Cade, D.L., "Sony Patents Contact Lens Cam with Zoom, Aperture Control, and More", PetaPixel, http://petapixel.com/2016/04/28/sony-patents-contact-lens-camera-joins-google-samsung/, Apr. 28, 2016, Accessed on Apr. 24, 2018, 8 pages.

Anthony, S., "Google invents smart contact lens with built-in camera: Superhuman Terminator-like vision here we come", ExtremeTech, http://www.extremetech.com/extreme/180571-google-invents-smart-contact-lens-with-built-in-camera-superhuman-terminator-like-vision-here-we-come, Apr. 15, 2014, Accessed on Apr. 24, 2018, 6 pages.

Webgazer.JS, "Democratizing Webcam Eye Tracking on the Browser", https://webgazer.cs.brown.edu/, Accessed on Apr. 24, 2018, 9 pages.

Wikipedia, "Google Glass", https://en.wikipedia.org/wiki/Google_Glass, Last edited on Apr. 4, 2018, Accessed on Apr. 24, 2018, 18 pages.

* cited by examiner

SMART CONTACT LENS SYSTEM WITH COGNITIVE ANALYSIS AND AID

FIELD

The present application relates generally to computers, computer devices, and computer applications, and more particularly to smart contact lens system with cognitive capabilities.

BACKGROUND

Smart lens technology has increased in capabilities and popularity over recent years. A modern smart lens involves extremely small versions of all the parts of a modern digital camera including an auto-focusing lens, a central processing unit (CPU), an antenna and even on-lens storage, wireless and smart device that utilizes Wi-Fi, Bluetooth or other communication standards, and provides features that include not only projecting video directly into the user's eyes but also connecting with an audio device. For example, capabilities may include features such as compatibility across a number of services and platforms, peer-to-peer connection through mesh networking, intelligent personal assistants, and the like. Each can have its own designated interface and features, usually launched or controlled based on eye movements and user activities via an application. Various eye-based control systems are also available, which may employ a gaze point tracking system or methodology that gathers signals from the eye and controls a device.

Using methodologies, for example, described above, a user can control various menus, navigate contents, and perform other actions on a device. But in such cases, the user needs to be within a threshold distance from the device employing the gaze point tracking, so that, for example, the gaze point tracking system can identify the eye-based signal. If the distance of the user from the device is more than a specified limit, then such gaze point tracking system may have difficulty in fetching and understanding the eye-based signals. If the distance of the user from the device is more than the threshold limit, the device may have some difficulty in tracking the eye signals. For example, if the user desires to control a television (TV) or another home network device from a distance, it may be desirable to have a method and system by which the user can control the devices seamlessly from that distance.

Smart lenses are used in many scenarios, and contain various sensors, including a front camera, a solar self-power unit, a light-emitting diode (LED) light, an antenna to connect to a mobile device, and/or a capability to sharing data. Existing smart contact lens systems, e.g., augmented reality (AR) and virtual reality (VR) systems further enable users to perform more intelligent actions by tracking and analyzing, for example, the movement of eyes, gestures, and images. Systems also may monitor the changes in the eye position and correlate the changes with the corresponding graphical elements, e.g., user interface (UI) component.

BRIEF SUMMARY

A method and system for smart contact lens may be provided. The method may be performed by at least one hardware processor communicating with a smart contact lens comprising at least a microprocessor, an image capturing lens, and a wireless communication interface. The method, in one aspect, may include receiving from the smart contact lens, data captured by the smart contact lens, the data associated with a user wearing the smart lens reading content item from a data source, the data comprising at least data representing eye movements of the user while reading the content item. The method may also include, based on the data, determining reading factors associated with the user with respect to the content item, the reading factors comprising at least a user's cognitive state determined at least from analyzing the data representing eye movements. The method may also include, responsive to determining that the user's cognitive state is above a threshold value, generating an assistive action associated with the content item. The method may further include transmitting a signal to at least one assistive device to perform the assistive action, wherein the assistive device performs the assistive action responsive to receiving the signal.

A smart lens system, in one aspect, may include at least one hardware processor communicatively coupled via a communication network to a smart contact lens comprising at least a microprocessor, an image capturing sensor, and a wireless communication interface. The at least one hardware processor may be operable to at least: receive from the smart contact lens data captured by the smart contact lens, the data associated with a user wearing the smart lens reading content item from a data source, the data comprising at least data representing of eye movements of the user while reading the content item. The at least one hardware processor also may be operable to, based on the data, determine reading factors associated with the user with respect to the content item, the reading factors comprising at least a user's cognitive state determined at least from analyzing the data representing eye movements. The at least one hardware processor also may be operable to, responsive to determining that the user's cognitive state is above a threshold value, generate an assistive action associated with the content item. The at least one hardware processor also may be operable to transmit a signal to at least one assistive device to perform the assistive action, wherein the assistive device performs the assistive action responsive to receiving the signal.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

A smart lens system, method and technique are disclosed, which provide a user reading assistance based on contextual analysis and content importance. Based on current user context and context item characteristics, a smart lens system may estimate the reading state of the user with respect to the content item and take an ameliorative action to pacify the reading state; enable cognitive assistive action associated with the content item using the reading factors of the learner; configure a user interface (UI) based on a user's conglomerate state and contextual situation; and learn to store or cache the important phrases or capture in a cloud database or similar repository in response to understanding the user's eye and gaze detection pattern and historical movements.

Figure 1:
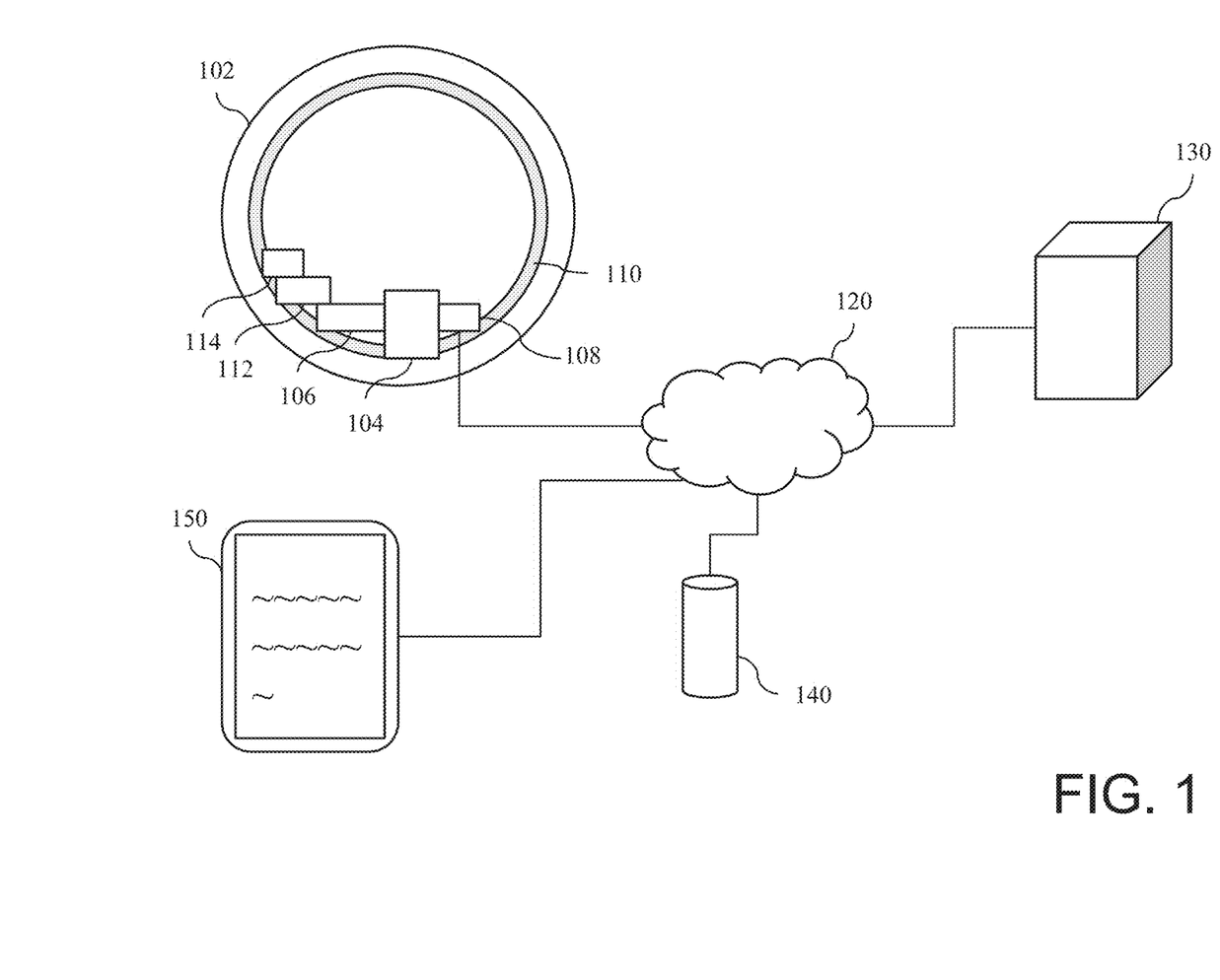
FIG. 1 is a diagram illustrating components of a smart lens system of the present disclosure in one embodiment.

FIG. 1 is a diagram illustrating components of a smart lens system in one embodiment of the present disclosure. A smart lens system may include a smart lens or device 102, which may include a microprocessor or a controller 104, an image capture device (e.g., including an image capturing sensor) such as a camera or the like device 106, a wireless communication interface 108, and an antenna 110. The smart lens system may include a computer or one or more hardware processors 130, for example, communicatively coupled to the smart lens 102, for example, and communicate with a microprocessor 104 of the smart lens 102, for example, via a communication network 120 such as, but not limited to, a wireless network. The smart lens system may also connect one or more hardware processors 130 to a voice-controlled intelligent personal assistant service or device 140. An example of a voice-controlled intelligent personal assistant service includes, but is not limited to, Amazon® Echo from Amazon.com, Inc., Seattle, Wash. The smart lens system and/or method may monitor user activities such as an eye movement, hand pointing movement, and/or facial expression, and/or other activities, with respect to a reading of a content item on a user device such as an electronic book, tablet, laptop, and/or another user device. In some embodiments, eye movements may be detected using video images from which the eye position is extracted. For instance, the smart lens 102 may capture, e.g., via the camera or like image capture device 106, eye movement images of the user reading content or content item from a user's reading device 150 such as a tablet, electronic book, or laptop, or another device. The microprocessor 104 of the smart lens 102 may transmit the captured images to the computer or one or more hardware processors 130. In some embodiments, the smart lens 102 or the microprocessor 104 of the smart lens may store the video or a series of images in its local storage or memory device 112. The smart lens 102 may also include one or more sensors 114 that detect various physiological states of a user wearing the lens. One or more hardware processors 130 may analyze the video or a series of images that capture the eye movement. User activities such as pupil dilation, glucose levels, head and/or body movements may be monitored and captured, for example, to detect a change in posture and reading environment context. Examples of reading environment context may include, for example, in an automobile setting, at a desk in a room, and/or another reading environment. Similarly, hand pointing movements, and/or facial expressions may be detected by capturing or obtaining a video or images and analyzing the video images with respect to the physiological movements or expressions of the user. In some aspects, the hand gestures and/or facial expressions are monitored by smart eye lens camera or an external Internet Protocol (IP) camera communicating with the smart lens 102 via a wireless module. The monitored and captured hand gestures and/or facial expressions data may be stored in a cloud repository.

Using monitored user activities, the system and/or method, for example, one or more hardware processors 130 may estimate one or more reading factors (e.g., confused state) of the user with respect to a content item, and using one or more of the estimated reading factors of the user, may generate at least one assistive action associated with a content item. The system and/or method may also include displaying at least one assistive action on a user computing device 150.

In various embodiments, a smart lens device 102 and/or one or more hardware processors 130 may be configured to monitor user engagements and interactions with the one or more content items. In some embodiments, one or more hardware processors 130 of a smart lens system may be configured to analyze an outcome of the user interactions (of the user wearing the smart lens 120) with the one or more content items viewed via the user's reading device 150. In some embodiments, one or more hardware processors 130 of a smart lens system may be configured to perform an action that assists the user such as, but not limited to, underlying (or marking) at least one word or phrase in the content viewable on the user's reading device 150 and/or triggering a voice-controlled intelligent personal assistant service 140 (e.g., AMAZON ECHO) to summarize a key concept of the current and previous pages in response to a determination of the user context analysis, for example, that indicated the user may be in a confused state with respect to the content that is read.

In way of example, based on the user's gestures or physiological movements (e.g., eye movement, hand pointing/movement, facial expression, and/or others), specific terms, phrases or concepts can be selected from the content that the user is reading or viewing. For example, an eye gaze tracking methodology may be employed to determine a location or area of the content the user is reading or viewing, to determine the specific terms or phrases. Facial expressions and hand gestures may be monitored and tracked via an external camera, which can communicate with the smart contact lens 102 via a nano-wifi module inbuilt in the smart contact lens 102 and store information in the cloud repository, for example, for caching purposes. In some aspects, the eye movement may be tracked by a nano-accelerometer inbuilt in the smart contact lens 102 and a magnetic sensor scanning the direction of focus of the eye. The dimensions of the eye lens monitored by inbuilt nano-camera may be used to determine the focal length and determine the focusing distance of the eye from the specific object being viewed. Context-specific responses are then generated and relayed back to the user. This can be an instance where the user's eye gaze traverses a term such as "ACL" in the content, and given the physiological response (e.g., a gesture that indicates the user is puzzled or confused, pupil dilation, or another physiological indication) the meaning of ACL can be determined in the context of the content the user is reading, for example, based on the user's location, user profile, domain expertise, and/or another attribute. For instance, if the user's profile or another attribute indicates that the user is a software engineer, one or more hardware processors 130 of the smart lens system in some embodiments may determine that ACL stands for "Access Control Layer" and not "Anterior Cruciate Ligament". For example, based on the images received from the smart lens 102, one or more hardware processors 130 may generate context specific response.

Figure 4:
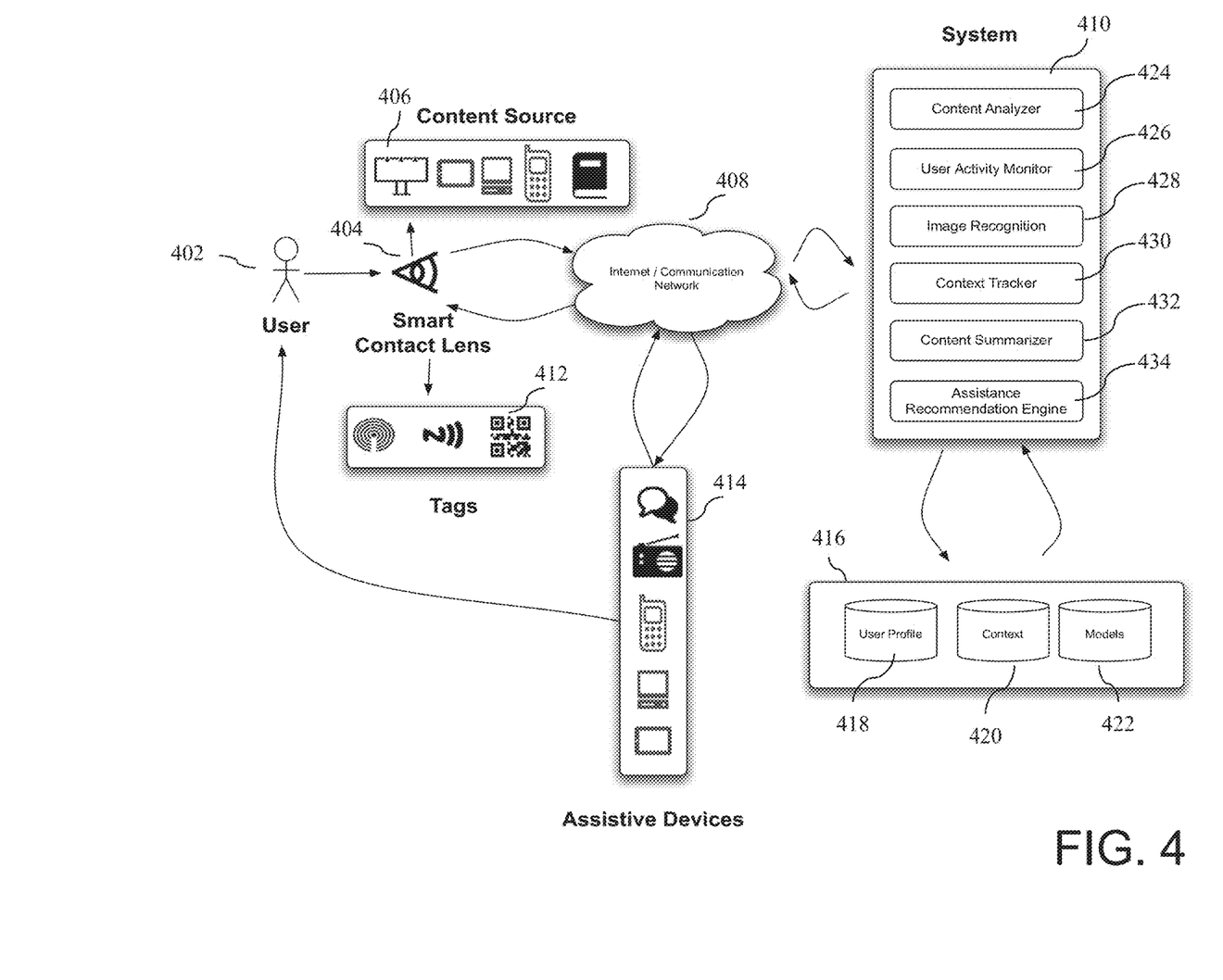
FIG. 4 is a diagram illustrating system components of a smart lens system of the present disclosure in one embodiment.

A smart lens system in some embodiments may determine interesting or context relevant information (topic or concept) by capturing data (e.g., text, image) from a user's primary reading computing device (e.g., tablet, electronic book, laptop, and/or another device) 150. Interesting or relevant content or information may be determined from the combination of features extracted from facial expressions (being monitored as explained above) and eye tracking performed by a smart contact lens camera (e.g., with accelerometer reading) and by storing the information in the cloud or reading device (e.g., which may be connected to the cloud). The user's account may be linked to the text or information being read and the cloud repository may get updated. The information updated in the cloud repository may be retrieved by the reading device. Real-time determination of interesting or context relevant information may be also performed via historic data mapping of interesting information based on information other users have found context relevant or interesting historically. The user activity monitoring component 426 may capture text and/or image data. A history of interesting text or image data may be stored in a local buffer memory 112 of the smart lens device, stored remotely in a remote storage device of a computing system 130 in association with an identifier of the smart lens device, or combinations of both. The history in some embodiments is configured to store captured text or image data and the corresponding identification of concepts presented in the text or image data as determined from the smart lens device, identified additional data source types, and any other suitable features of the captured text or image, for a predetermined time window, or period of time, consistent with an amount of time required to identify events occurring within or in association with the monitored reading content and context. For example, a time window may be set to store text or image data captured over a 3, 6, or 9-minute time duration, or any other desirable amount of time, such that patterns and correlations of data present in the text or image data captured during the time window may be made to identify events occurring within or associated with the monitored reading content and context. The analysis of the captured information in some embodiments is used to assist the user at a particular time t in the near future, e.g., responsive to detecting a similar or related concept.

The following describes an example use case. A user wearing a smart lens 102 is reading a book or reading on the user's reading device 150 such as a tablet, electronic book, laptop or another device. A smart lens device 102 in some embodiments, based on tracking the user's eye movements, for example, including reading speed, determines and stores for a period of time T, content items that are determined to be interesting or pertain to the main topic of the content the user is reading. For example, from a combination of facial expressions and/or hand gestures monitored by an external camera in the surroundings in conjunction with eye tracking may determine the interesting or main topic. In addition, user data may be mapped to information that other users have found context relevant or interesting historically. This can be recommended using recommendation algorithms like collaborative filtering or via text similarity. Consider that the user leaves the reading environment for a period or duration of time. For example, the user stops reading for some time, for instance, on the reading device 150. The user then returns to the reading device 150 and picks up to continue the user's reading. The smart lens system may detect that the user is in confused state. For example, the smart lens system (e.g., one or more hardware processors 130) may detect that the user is looking for a position in the reading material where the user has left reading, for example stopped or paused reading, on the reading device 150, based on the analysis of smart lens' captured images of user's eye movements, which for example, the smart lens 102 transmits to one or more hardware processors 130. The smart lens system in one embodiment of the present disclosure points the user to where the user has left off reading (the point where the user has previously stopped or paused), for example, by highlighting the point or by any other visual indication on a display screen of the device 150, and displays summarized information about his past reading. For example, one or more hardware processors 130 may communicate with the user's device on which the user is reading the content, and transmit a signal or signals to cause the user's device 150 to highlight or otherwise mark the location of the content where the user has previously left off, stopped or paused from reading. One or more hardware processors 130 may do so, for instance, responsive to comparing the measured confusion state (or cognitive state) to a predefined threshold value and determining that the measured confusion state is above the predefined threshold value. In some embodiments, the microprocessor 104 of the smart lens device may perform the above-described processing performed by one or more of the hardware processors 130.

In some embodiments, the "confused state" or cognitive state of the user may be determined based on a plurality of indicators (e.g., eye movement, hand pointing/movement, facial expression, and/or another gesture) that can be extracted from real-time and historical data. The indicators may be detected by, for example, tracking eyes' movement pattern, detecting user's hand movement or pointing direction, learning from the facial expression, and/or others. Based on the detected user confused state, one or more hardware processors 130 (and/or the smart lens device 102 (or a microprocessor 104 coupled with a smart lens device)) may further determine approximated location or area where the user has left off or stopped or paused reading. In some embodiments, the approximated location or area is further highlighted (e.g., color coded, temporarily underlined, or by another visual indication) by the user's device 150, responsive to receiving a signal or instructions from one or more hardware processors 130 and/or from the smart lens 102, for example, via the communication network 120. For instance, providing visual indication may also include automatically selecting or changing graphical elements by, for example, shifting images to the center on a given display, magnifying images, increasing or decreasing the brightness of color of images.

Figure 2:
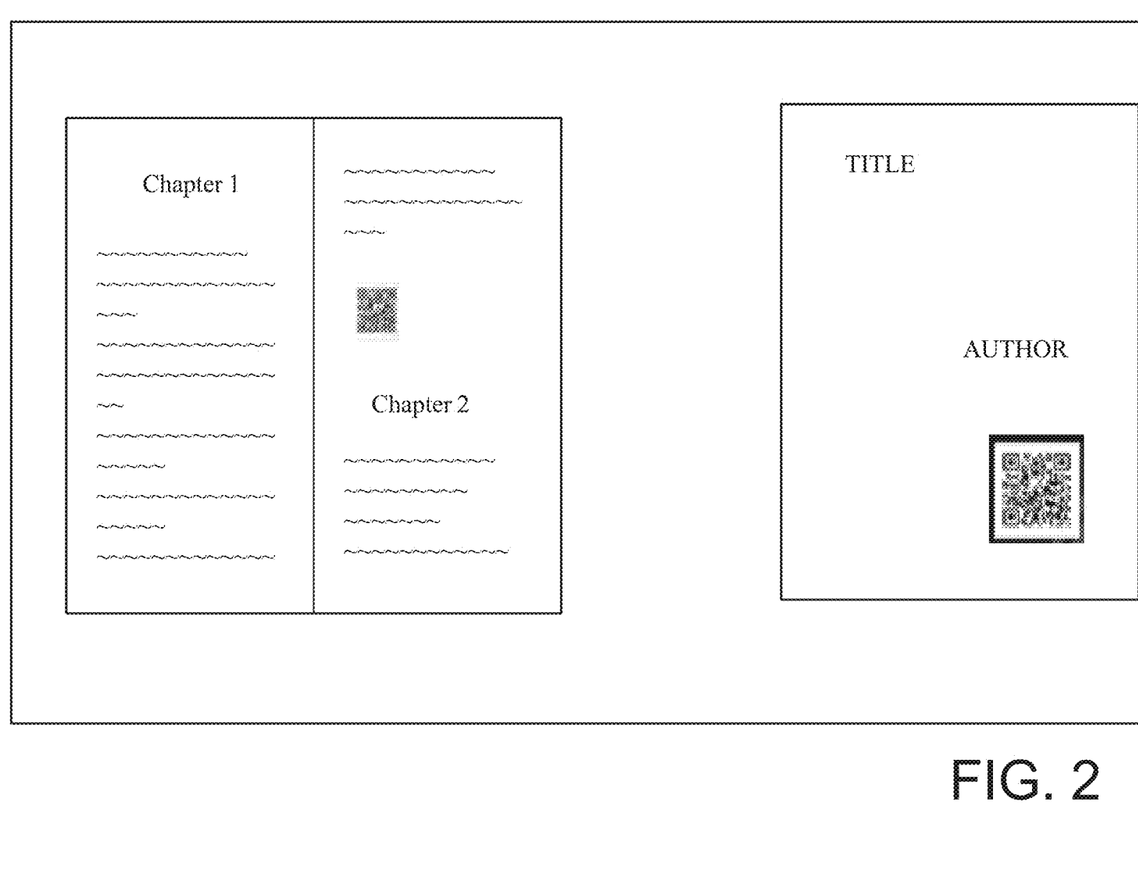
FIG. 2 shows an example illustration of a book embedding a QR code on a specific paragraph in the book in embodiment.

In some embodiments, the user's attention, fixation, activity, and state (e.g., confused) may be monitored, tracked and mapped to specific content, images, or information the user is reading or viewing. The methodology of the present disclosure in some embodiments is able, using identifiers like Quick Response (QR) code, Near Field Communication (NFC) tag, and/or iBeacon, to duplicate the content and/or image and the user's reaction, response and activity to specific content. Content producers, advertisers, authors, and/or artists, may want to receive feedback on that specific content. For example, FIG. 2 shows an example illustration of a book embedding a QR code on a specific paragraph in the book. Such data or book content may be displayed in electronic format, for example, in a reading device, monitor or screen, digital advertising billboards. Once the user reads the paragraph, the user would see the QR code and the user's physiological response and the content may be generated and relayed, for example, to be stored in a computer system accessible by those interested in the feedback, for example, stored in a database. A QR code scanner can determine the section of the book and can also be extended to be associated with Uniform Resource Locator (URL) information to display the user's response or feedback pertaining to that specific section or paragraph. For example, a microprocessor 104 of the smart lens and/or one or more hardware processors 130 may generate and store or cause to be stored, the user's physiological response to the content. In the database, the information generated and relayed may be stored in some embodiments in the following data structure or tuple format.

Content_User_Response=<User_ID, Content_ID, {Responses}>

For example: Content_User_Response=<1231, 54fc3, {confusion=0.1, alertness=0.4, reading_speed=56, pupil_dilation=0.45}>

Using this data, content producers can change the layout, explanation, clarity, and/or another aspect of the content to make the content more understandable and amenable to a user's understanding. This data can also be used to segment users and understand how they respond to specific content and stimuli.

In some embodiments, readers may be segmented based on their reading patterns (e.g., revisiting other pages for clarifications), monitored activities (e.g., eye tracking, facial expressions, pupil dilations), use of assistive actions (e.g., concept explanations). In some embodiments, smart eye lens tracking with an identifier of the reader's eye and specific cloud repository for each user performs the segmentation based on storing the credentials of the user and associating it with the respective cloud repository. In some embodiments, the content analyzer 424 and content summarizer 432 may perform the segmentation function. This segmentation information can be used to update the layout of content to improve specific user's reading experience. For example, notes sections may be added to the content that explain concepts that were searched for by similar users; links may be added to related content pages similar users referred to while reading a section. In some embodiments, the smart contact lens stores information pertaining to user's cognitive state and context, for example, in the respective cloud repository. For example, the wi-fi module inbuilt in the smart contact lens may interact with specific user's data, for example, in a cloud repository and may perform this adding. In some aspects, publishers of the content may utilize the information and add the information to the content. For example, publishers may have the ability to use this information to improve the layout and also add additional information to improve the reading experience based on a user's segment. In another aspect, content publishers may be able to also leverage the segmentation and/or feedback data to improve layout of their physical books in future editions for better reading experiences.

In some embodiments, a method of determining the approximated location or area of the reading material may use additional data that may be captured by the smart lens device from one or more secondary data sources while the user is away from the primary reading material for a period of time or duration. By way of examples, the user may have left the primary reading material to find a reference, keywords used to search on search engine (e.g., to find additional reference). The additional data may further include detecting from spoken words, using a speech recognition technique, that the user asked a nearby user or smart computing device such as an intelligent personal assistant that uses voice queries and natural language user interface. Secondary components like external IP cameras, sensors detecting the motion of users like pointing to different areas and performing functions such as changing channels, switching the speed of fan, turning on/off lights with user gestures may be recorded and correlated to the smart contact lens by means of training. An external camera with speech recognition engine may capture the user activities and correlate to smart contact lens, which may be connected via a wi-fi chip or processor to a cloud repository. Additionally, the smart contact lens may be able to determine task-switching (moving from primary reading source to a secondary), and determine and correlate that the keyword or concept being searched relates to a keyword or concept recently read on the primary reading source.

A method of summarizing information that is presented to the user responsive to determining that the user's confused state is above a threshold value, in some embodiments, may be based on analyzing the stored interesting or context relevant information, for example, which may be stored remotely in a remote storage device of a computing system in association with an identifier of the smart lens device, and the additional data captured by the smart lens device from the one or more secondary data sources, which also may be stored remotely in a remote storage device of a computing system in association with an identifier of the smart lens device.

One example of a summarization algorithm is an Attentional Encoder-Decoder Recurrent Neural Network summarization algorithm that finds the information deemed most important to the user for example, key clauses, sentences and/or paragraphs.

A summarization algorithm in some embodiments finds key concepts and key entities in the content by applying part-of-speech taggers, and word-embeddings-based representation of the input content and capturing additional linguistic features such as named-entity tags, and term frequency (TF) and inverse document frequency (IDF) statistics of the words. The summarization algorithm then creates an additional look-up based embedding matrices for the vocabulary of each tag-type, similar to the embeddings for words. For each word in the content, the summarization algorithm looks up the word's embeddings from all of its associated tags and concatenates them into a single long vector, for example, as shown in FIG. 3.

Figure 3:
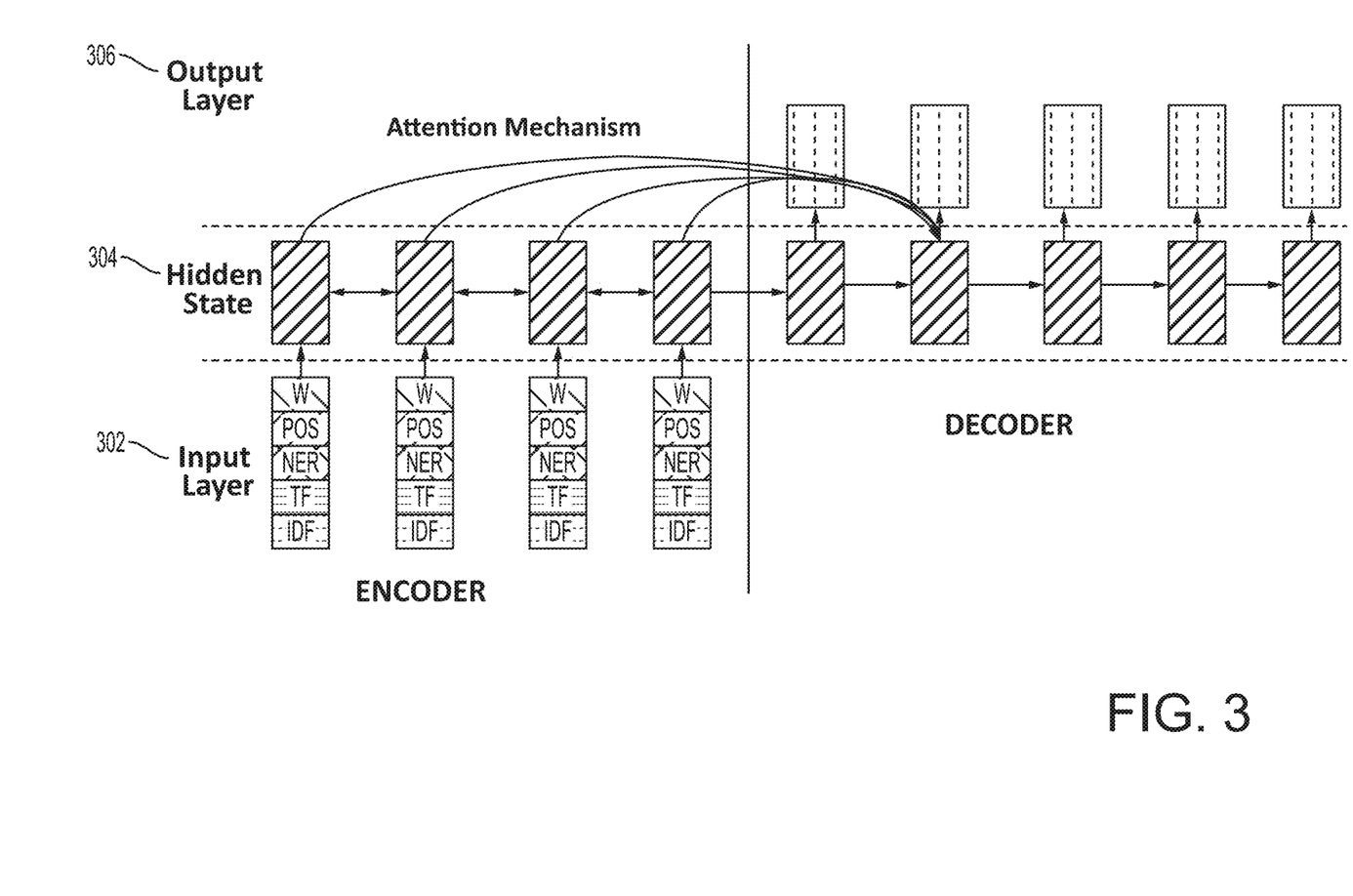
FIG. 3 shows a feature-rich-encoder of the present disclosure in one embodiment.

FIG. 3 shows a feature-rich-encoder in one embodiment of the present invention. The system and method of the present disclosure in some embodiments uses one embedding vector each for POS, NER tags and discretized TF and IDF values, which are concatenated together with word-based embeddings as input to the encoder, for example, as shown at 302. The output 304 is the summarized content. Each hidden layer box in the hidden layers 304 represents a node in the autoencoder. The hidden layers 304 transform the inputs into something that the output layer 306 can use. The output layer 306 transforms the hidden layer activations into desired output (e.g., summarized content, categorization).

Referring to FIG. 1, in some embodiments, a smart lens device 102 may include a text and image capture device 106 (e.g., inbuilt smart lens camera, which may capture text and images), and one or more processors 130 may process text and image sample data captured by the text and image capture device 106, and implement smart lens system logic. In some embodiments, the microprocessor 104 of the smart lens 102 may process the text and image sample data and implement smart lens system logic. Smart lens system logic of the smart lens system may receive, from the text and image capture device of the smart lens device, a text and image sample captured from monitored primary and secondary reading environments. The primary reading environment refers to the main focus of the user's initial attention (e.g., reading content on device, book, display, or another device); the secondary reading environment refers to the user undertaking a secondary task like searching for a reference or asking voice-controlled device (e.g., AMAZON ECHO) for assistance. The smart lens system logic may also cognitively summarize a text and image in the text and image sample data as a type of text/image based on performing a natural language processing of a plurality of different characteristics of the text/image and matching results of the natural language processing to criteria specified in a plurality of text and image models. The smart lens system logic may also determine, based on the summarization of the text and image, whether an assistive action is to be performed based on the summarization of the text and image. In response to determining that an assistive action is to be performed, the smart lens system logic may initiate a performance of the assistive action. The smart lens system accordingly performs the assistive action.

The user context analysis may indicate that the user had slow progress reading a particular segment of the content involving one or more themes/topics. The smart lens system logic in some embodiments further learns an inter-page reading progress pattern to determine what action to generate for assisting the user.

To understand reading complexity and difficulty, in one implementation, the smart lens system may use a variant of Gunning Fog Index function. A Gunning fog index may be requested for content read or viewed. In linguistics, the Gunning fog index measures the readability of English writing. Texts for a wide audience generally need a fog index less than 12. Texts requiring near-universal understanding generally need an index less than 8. A request can be made by the user or third party.

The complete formula such as the following may be used:

$$0.4\left[\left(\frac{words}{sentences}\right) + 100\left(\frac{complex\ words}{words}\right)\right]$$

In the Flesch reading-ease test, higher scores indicate material that is easier to read; lower numbers mark passages that are more difficult to read. The formula for the Flesch reading-ease score (FRES) test is:

$$206.835 - 1.015\left(\frac{total\ words}{total\ sentences}\right) - 84.6\left(\frac{total\ syllables}{total\ words}\right)$$

FIG. 4 is a diagram illustrating system components of a smart lens system in one embodiment of the present disclosure. Based on the content 406 the user reads and/or views, along with their context such as the user profile 418 which may include demographic and preference data, the reading location of the content and other context data 420, the physiological states (e.g., tired, confused, asleep, or another) and codes and identifiers like QR Codes, NFC Tags, barcodes, iBeacon 114, the smart lens system may process and generate one or more assistive actions via devices 414, which may enhance the user experience and/or provide content providers with additional information about their users' engagement.

For instance, a user 402 wearing or using a smart lens 404 on the user's eyes, for example, reads or views content, e.g., from a book, magazine, tablet, phone, billboard, and/or another device, for example, shown at 406. The smart lens 404 captures the user's activities, for example, eye gazes, eye movements, for example, via one or more sensors coupled with the smart lens 404. The smart lens 404 may also capture the user's other physiological activities such as hand and finger movements. In some embodiments, the smart lens 404 may determine user activities by capturing a text, video or a series of images of the user's eye movement, and/or other physiological movement. The smart lens 404 also captures any bar codes or other tags 412 associated with the content the user is currently reading or viewing on a user's reading device 406, for example, user's electronic book or another device. The information captured by the smart lens 404 is transmitted, e.g., via a communication network 408, to one or more hardware processors 410 that implement smart lens system logic.

The smart lens system logic may include content analysis at 424, user activity monitoring at 426, image recognition at 428, context tracking at 430, content summarizing at 432, and assistance recommendation 434. The smart lens system logic may be implemented and execute on one or more hardware processors. In another aspect, some of the smart lens system logic may be executed by the smart lens 404 locally utilizing one or more microprocessors and memory devices coupled locally in the smart lens. Based on user's context 420, profile 418 and models 422, with the content the user is reading and/or viewing (captures by the smart lens 404), the smart lens system logic provides personalized experience to the user 402 reading or viewing the content 406, for example, in real-time. The models 422 may include one or more neural network models. For instance, the cognitive state of the user, in conjunction with other parameters like user's context, location, previous content summarized, gestures defined, may be determined and fed as inputs to a neural network classifier model in order to determine the learnt content and new information gathered from above features like other gestures learnt, which can be utilized by the user.

Content analysis at 424 may include analyzing content the user is reading or viewing. Content analyzer 424 may include the portion the user is currently reading and information about content which would be interesting to the user based on user's previous preferences, cognitive state, which was modeled via neural network classifier model or another machine learning classifiers to determine the future interesting content or context. Actions or functions can include predictive content summarization or highlighting after determining users' historical preferences pertaining to the content. User activity monitoring at 426 may include receiving real-time captured information or data associated with user activities, for example, eye movements, hand movements, and/or other physiological data from the smart lens 404, for example, continuously or periodically. Image recognition processing analyzes images captured by the smart lens 404, e.g., of user's physiological movements such as eye movements, and analyzes the images in determining the user's cognitive states such as whether the user is confused or puzzled, tired, and/or other states. In some aspects, confused state may be examined by facial micro-expressions which can be detected by an external camera interacting with the smart contact lens and predicting the cognitive state of the user.

Context tracking 403, for example, may include determining and tracking the user's cognitive states based on the image analysis performed by image recognition. Context tracker 403 may correlate the activity being performed by the user with respect to the cognitive state. Content summarizing 430 may summarize the content the user is viewing. Assistance recommendation at 434 may determine and/or generate an action to perform based on the user's cognitive state with context 420, profile 418, and/or other information, to help the user 402 in continuing to read and/or view the content. In some embodiments, assistance recommendations can be generated via supervised algorithms such as neural networks, support vector machines (SVMs), and/or another machine learning algorithm or classifier, collaborative filtering, k-means and/or unsupervised methods. For example, the confused state of the user may be compared to a threshold value, and if the confused state exceeds the threshold value, an assistive action may be generated. Assistance recommendation at 434 also may include transmitting a signal or data to one or more assistive devices 414 such as an intelligent personal assistance, the user's reading device (e.g., a content source 406), and/or other assistive devices, to trigger an assistive device to perform the action. In some embodiment, one or more assistive devices may relay content and exploratory content. Exploratory content refers to content, which may confuse the user, for example, determined based on facial expressions, or may be interesting to the user, for example, determined based on previous pattern history which was marked or annotated by the user or learnt by the smart contact lens. Exploratory content may also include topical content that the user can review to better understand the topic or subject area. The content relayed may include a definition of a term, relevant links, references, videos, or another content. Examples of assistive devices 414 may include, but are not limited to, computer-implemented conversational agent, intelligent personal assistant, on-device messaging service or app, instant messaging app, and an audio device.

Figure 5:
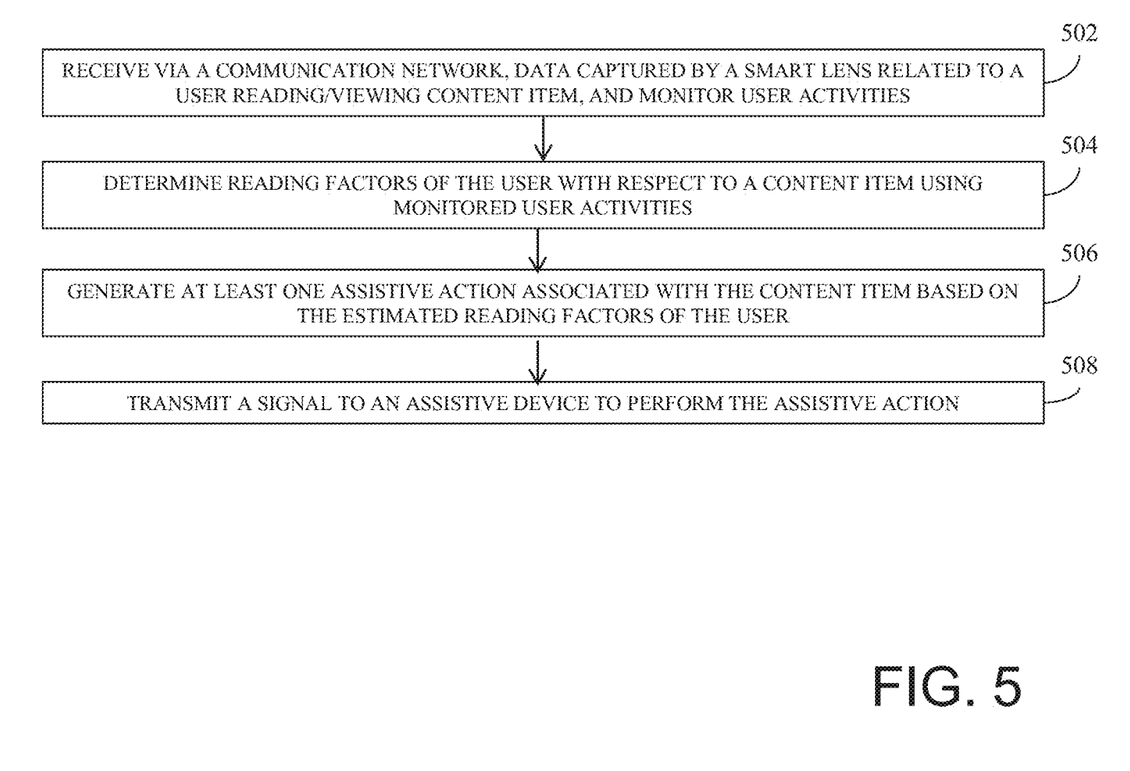
FIG. 5 is a flow diagram illustrating a method of a smart lens system of the present disclosure in one embodiment.

FIG. 5 is a flow diagram illustrating a method of a smart lens system in one embodiment of the present disclosure. The smart lens system in some embodiments may provide an automated or autonomous user reading assistance based on contextual analysis and content importance. The smart lens system, for example, as shown in FIG. 1, may include a smart lens, image processing capability and system logic, and may also be communicatively connected to a voice-controlled intelligent personal assistant device or service. Referring to FIG. 5, at 502, the method may include receiving data captured by a smart lens and monitoring user activities with respect to reading of a content item on a user device such as a table, electronic book, laptop, or another device. Monitoring user activities may include detecting eye movements, hand pointing or movement, facial expression, pupil dilation, glucose levels, head and/or body movement, which may allow for detecting a change in posture, reading environment context (e.g., reading at a desk or in a confined area such as an automobile as a passenger in the automobile). For example, data such as images captured by a smart lens worn or used by a user may be received and based on the performing image recognition analysis, the user activities may be monitored. One or more hardware processors perform the monitoring. Low glucose levels have been shown to result in difficulty focusing, lack of awareness which impacts the user's ability to concentrate on content and fully comprehend it. By detecting and logging troughs of low glucose levels, it can be inferred that the content the user is reading might not have been fully assimilated, or that there is an opportunity to trigger an assistive action.

At 504, the method may include estimating reading factors of the user with respect to a content item using monitored user activities. Examples of the reading factors may include, but are not limited to, a user context (e.g., a degree of engagement between the user and the content item, engagement patterns between the user and the content item, understanding level of the user with respect to the content item, a reading progression state of the user with respect to the content item, a degree of the user confusion state with respect to the reading content item, and reading environment context), a user profile (which may specify user skill, knowledge, one or more user preferences and/or other information), and content item characteristics (which may specify complexity level, importance level, and/or other attributes associated with the content item). The content items monitored (e.g., on devises) may be relayed from the device or digitized using optical character recognition (OCR) techniques. This provides the text to the content item and one or more techniques such as Flesch reading complexity text, may be applied to the text.

In some embodiments, user context may be determined by estimating or determining one or more of the degree of engagement between the user and the content item, engagement patterns between the user, understanding level of the user with respect to the content item, a reading progression state of the user with respect to the content item, the degree of the user confusion state with respect to the reading content item, and the reading environment context (e.g., location where the user may be performing the reading), which may be predicted. Information captured by an external camera and by monitoring user's activities along with user's cognitive state may be used to correlate the user's direction gathered from smart contact lens. Such correlated information may be used to predict the level of engagement or interest of the user with regard to the activity. The computed cognitive state and activity correlation may be stored in a cloud repository or another repository, with threshold levels pertaining to a degree of confusion/engagement level. Such information helps in predicting the next set of actions of the predicted user's context.

User context may also include approximated location or area where the user has probably left or stopped or paused reading. In some embodiments, determining the approximated location or area of the content (or content item) where the user has left or stopped or paused reading include using one or more secondary data sources while the user is away from the primary reading material for a period of time or duration. In some embodiments, the approximate location is determined by the smart contact lens which has the eye lens tracker, for example, being performed by nano-accelerometer, miniature camera and magnetic sensor for determining the focal length, direction of focus and capturing the content. The content may be stored in a cloud repository or another repository, for example, via wifi or another wireless communication device, for example, located in the smart contact lens interacting with a server, for example, a cloud server.

In some embodiments, the reading factors may be determined periodically (e.g., every 30 seconds), based on a time series of data captured by the smart lens. For instance, the times series of data in a time window (e.g., duration of 30 seconds) may be stored, and analyzed at time intervals (e.g., every 30 seconds) to determine user factors in real-time. In some aspects, polling is possible and polling after sporadic or regular time intervals reduces power consumption. Polling can be configured with more time intervals depending on user's preferences. This methodology, in one aspect, may reduce the amount of the captured data that need to be stored in memory at a time. In one aspect, only a few number of the time windows previously captured need be saved in memory, with the older data moved to another storage device in memory/storage hierarchy.

The smart lens system may also detect that the user is away from the primary reading material for a period of time or duration. For example, to detect that the user is away from the primary reading material, the smart lens system may analyze at least one keyword used to search on a search engine or at least one voice command used to request voice-controlled user device. For instance, the smart lens system may detect that the user is performing a keyword search on an Internet search engine, for example, via a web browser on the user's computing device, whether on the primary reading device or another device, for example, because the user desires to find additional reference. For instance, a built-in smart contact lens camera may record user activities, for example, user performing a keyword search, and such user activities may be monitored. To detect that the user is away from the primary reading material, the smart lens system may also detect from the user's spoken words using speech recognition techniques that the user asked a nearby user or smart computing devices, such as an intelligent personal assistant service or device. For instance, mobile or wearable devices capable of performing speech recognition may include a module which can communicate or relay information to the smart contact lens. The mobile or wearable devices and the smart contact lens may all interact with the user's cloud repository or another repository storing information in a server such as the cloud server for the specific user.

At 506, the method may include generating at least one assistive action associated with the content item based on the estimated reading factors of the user. Estimated reading factors contribute to computing of the degree of user's confused state, which may trigger an assistant action responsive to meeting a pre-defined threshold level.

In some embodiments, an assistive action is generated responsive to determining that the user's confused state meets or is above a threshold value. The threshold value may be configurable.

Examples of an assistive action may include, but are not limited to, marking (such as underlining, highlighting, or providing another indication) a word, sentence, phrase or a portion of the content the user is or was reading; summering a portion of a content item; and triggering a sound-controlled intelligent personal assistant service. The assistant service, for example, can fetch or store relevant data, keywords, phrases in a repository such as a cloud repository or data storage. The assistant service understands the action that needs to be performed based on a set of keywords or facial expressions and cognitive state detected by external devices in order to summarize or highlight content or adjust light brightness in the device or surroundings based on the user's activity and previous actions/pattern history.

At 508, the method may include triggering or causing to display at least one assistive action on a computing device or causing an assistive action to be displayed on a computing device. For instance, responsive to determining an assistive action, the smart lens system may transmit a signal and/or data to a computing device such as an assistive device, for example, via a communication network, to present or perform the assistive action. An assistive device in this aspect, for example, may also include the user's reading device, which may receive a signal to highlight a word or phrase appearing in, or a portion of, the content the user is reading or viewing.

In some embodiments, the method may also include configuring the smart lens system. Configuring the smart lens system may include storing text or image data and the corresponding identification of concepts present in the text or image for temporary duration. Configuring the smart lens system may also include identifying additional data source types, and any other suitable features of the captured text or image, for a predetermined time window, or a period of time, consistent with an amount of time required to identify events occurring within or in association with the monitored reading content and context.

Figure 6:
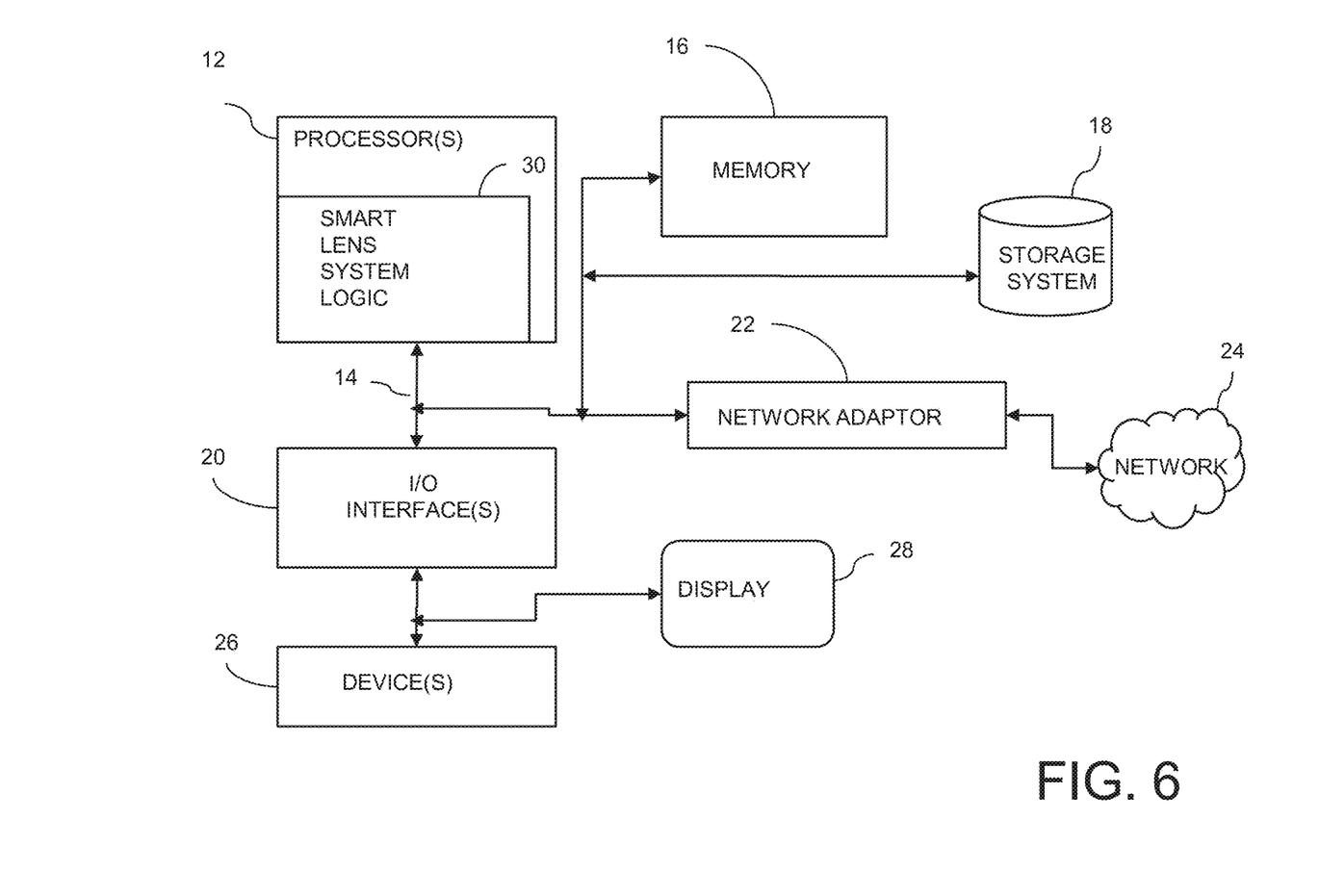
FIG. 6 illustrates a schematic of an example computer or processing system that may implement smart lens system logic of the present disclosure in one embodiment.

FIG. 6 illustrates a schematic of an example computer or processing system that may implement smart lens system logic in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A method executed by at least one hardware processor communicating with a smart contact lens comprising at least a microprocessor, an image capturing lens, and a wireless communication interface, the method comprising:
   receiving from the smart contact lens, data captured by the smart contact lens, the data associated with a user wearing the smart lens reading content item from a data source, the data comprising at least data representing eye movements of the user while reading the content item;
   based on the data, determining reading factors associated with the user with respect to the content item, the reading factors comprising at least a user's cognitive state determined at least from analyzing the data representing eye movements;
   responsive to determining that the user's cognitive state is above a threshold value, generating an assistive action associated with the content item;
   transmitting a signal to an assistive device to perform the assistive action, wherein the assistive device performs the assistive action responsive to receiving the signal; and
   capturing content from the data source in time windows, the captured content being stored as a history of content items read by the user, the history of content items being used in the assistive action to assist the user with reading the content item,
   the assistive action including summarizing the content item based on the captured time windows of the content.

2. The method of claim 1, wherein the data further comprises images of the user's hand movement, facial expression, head movement while reading the content item, glucose level, and pupil dilation.

3. The method of claim 1, wherein the reading factors further comprises user context, user profile and characteristics associated with the content item.

4. The method of claim 1, wherein the assistive action comprises at least one of highlighting a portion of the content item on a display of the data source from which the user is reading the content item, triggering a sound-controlled intelligent personal assistant service.

5. The method of claim 1, wherein the reading factors further comprises user context, wherein the user context comprises at least one of a degree of engagement between the user and the content item, an engagement pattern between the user and the content item, a degree of the user's confusion state with respect to the reading of the content item, and the user's reading environment context.

6. The method of claim 1, further comprising determining an area in the content item where the user has left reading to generate the assistive action.

7. The method of claim 1, further comprising storing the data for temporary duration for a predetermined time window.

8. A smart lens system comprising:
   at least one hardware processor communicatively coupled via a communication network to a smart contact lens comprising at least a microprocessor, an image capturing sensor, and a wireless communication interface, the at least one hardware processor operable to at least:
   receive from the smart contact lens data captured by the smart contact lens, the data associated with a user wearing the smart lens reading content item from a data source, the data comprising at least data representing eye movements of the user while reading the content item;
   based on the data, determine reading factors associated with the user with respect to the content item, the reading factors comprising at least a user's cognitive state determined at least from analyzing the data representing eye movements;
   responsive to determining that the user's cognitive state is above a threshold value, generate an assistive action associated with the content item;
   transmit a signal to at least one assistive device to perform the assistive action, wherein the assistive device performs the assistive action responsive to receiving the signal; and
   capturing content from the data source in time windows, the captured content being stored as a history of content items read by the user, the history of content items being used in the assistive action to assist the user with reading the content item, the assistive action including summarizing the content item based on the captured time windows of the content.

9. The system of claim 8, wherein the data further comprises images of the user's hand movement, facial expression, head movement, glucose level, and pupil dilation while viewing the content item.

10. The system of claim 8, wherein the reading factors further comprises user context, user profile and characteristics associated with the content item.

11. The system of claim 8, wherein the assistive action comprises at least one of highlighting a portion of the content item on a display of the data source from which the user is reading the content item, triggering a sound-controlled intelligent personal assistant service.

12. The system of claim 8, wherein the reading factors further comprises user context, wherein the user context comprises at least one of a degree of engagement between the user and the content item, an engagement pattern between the user and the content item, a degree of the user's confusion state with respect to the reading of the content item, and the user's reading environment context.

13. The system of claim 8, further comprising determining an area in the content item where the user has left reading to generate the assistive action.

14. The system of claim 8, further comprising storing the data for temporary duration for a predetermined time window.

15. The system of claim 8, wherein the assistive device comprises at least one of an intelligent personal assistant device, an electronic book, a laptop, an audio device, a smartphone, and a device running an instant messaging app.

16. A computer readable storage medium storing a program of instructions executable by a machine to perform a method of executed by at least one hardware processor communicating with a smart contact lens comprising at least a microprocessor, an image capturing sensor, and a wireless communication interface, the method comprising:

receiving from the smart contact lens data captured by the smart contact lens, the data associated with a user wearing the smart lens reading content item from a data source, the data comprising at least data representing eye movements of the user while reading the content item;

based on the data, determining reading factors associated with the user with respect to the content item, the reading factors comprising at least a user's cognitive state determined at least from analyzing the data representing eye movements;

responsive to determining that the user's cognitive state is above a threshold value, generating an assistive action associated with the content item;

transmitting a signal to at least on assistive device to perform the assistive action, wherein the assistive device performs the assistive action responsive to receiving the signal; and capturing content from the data source in time windows, the captured content being stored as a history of content items read by the user, the history of content items being used in the assistive action to assist the user with reading the content item, the assistive action including summarizing the content item based on the captured time windows of the content.

17. The computer readable storage medium of claim 16, wherein the data further comprises images of the user's hand movement, facial expression, head movement while reading the content item, glucose level, and pupil dilation.

18. The computer readable storage medium of claim 16, wherein the reading factors further comprises user context, user profile and content item characteristics associated with the content item.

19. The computer readable storage medium of claim 16, wherein the assistive action comprises at least one of highlighting a portion of the content item on a display of the data source from which the user is reading the content item, triggering a sound-controlled intelligent personal assistant service.

20. The computer readable storage medium of claim 16, wherein the reading factors further comprises user context, wherein the user context comprises at least one of a degree of engagement between the user and the content item, an engagement pattern between the user and the content item, a degree of the user's confusion state with respect to the reading of the content item, and the user's reading environment context.

* * * * *